United States Patent
Coughlan et al.

(10) Patent No.: US 9,855,238 B2
(45) Date of Patent: Jan. 2, 2018

(54) COMPOSITIONS COMPRISING 15-HEPE AND METHODS OF USING THE SAME

(71) Applicant: Afimmune Limited, Dublin (IE)

(72) Inventors: David Coughlan, Dublin (IE); John Climax, Dublin (IE)

(73) Assignee: AFIMMUNE LIMITED (IE)

( * ) Notice: Subject to any disclaimer, the term of this patent is extended or adjusted under 35 U.S.C. 154(b) by 0 days.

(21) Appl. No.: 15/383,889

(22) Filed: Dec. 19, 2016

(65) Prior Publication Data

US 2017/0172965 A1 Jun. 22, 2017

Related U.S. Application Data

(60) Provisional application No. 62/269,280, filed on Dec. 18, 2015.

(51) Int. Cl.
*A61K 31/202* (2006.01)
*A61K 31/232* (2006.01)

(52) U.S. Cl.
CPC .......... *A61K 31/202* (2013.01); *A61K 31/232* (2013.01)

(58) Field of Classification Search
None
See application file for complete search history.

(56) References Cited

FOREIGN PATENT DOCUMENTS

| EP | 2762143 | 8/2014 |
|---|---|---|
| JP | H05186342 | 7/1993 |
| WO | WO2014/019919 | 2/2014 |
| WO | WO2015/071766 | 5/2015 |
| WO | WO2016/090030 | 6/2016 |
| WO | WO2016/113635 | 7/2016 |
| WO | WO2016/181221 | 11/2016 |
| WO | WO2017/013492 | 1/2017 |

OTHER PUBLICATIONS

Desbois et al., Marine Drugs (2013), 11(11), pp. 4544-4557.*
Mitchell et al., Biochemical Society Transactions (1984), 12(5), pp. 839-841.*
Partial International Search Report dated Mar. 24, 2017 for Internatioanl Application No. PCT/IB16/01878.

* cited by examiner

*Primary Examiner* — Brian J Davis
(74) *Attorney, Agent, or Firm* — Perkins Coie LLP

(57) ABSTRACT

The present invention relates to the compositions comprising 15-HEPE and methods of treatment relating to same.

6 Claims, 5 Drawing Sheets

COMPOSITIONS COMPRISING 15-HEPE AND METHODS OF USING THE SAME

PRIORITY CLAIM

This application claims priority to U.S. Provisional Application No. 62/269,280, filed Dec. 18, 2015, which is incorporated herein by reference in its entirety.

TECHNICAL FIELD

The present disclosure provides compositions, formulations and methods of treating or preventing a disease by administering a pharmaceutical composition comprising 15-hydroxyeicosapentaenoic acid (also referred to as 15-HEPE or 15-OHEPA) to a subject in need thereof.

SUMMARY

In various embodiments, the invention provides compositions and formulations comprising 15-hydroxy eicosapentaenoic acid (hereinafter "15-HEPE") and methods of treating diseases and disorders using the same. The compositions and formulations disclosed herein may be used in the treatment of liver disease, arthritis, fibrosis, idiopathic pulmonary fibrosis, impaired insulin sensitivity, psoriasis, cancer (e.g. melanoma), neurodegenerative disorders (e.g. Huntington's disease), inflammatory diseases, adipocyte differentiation, fertility or reproduction issues, pain, obesity, and their sequelae, among other diseases and disorders.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology.

DETAILED DESCRIPTION

Figure 1:
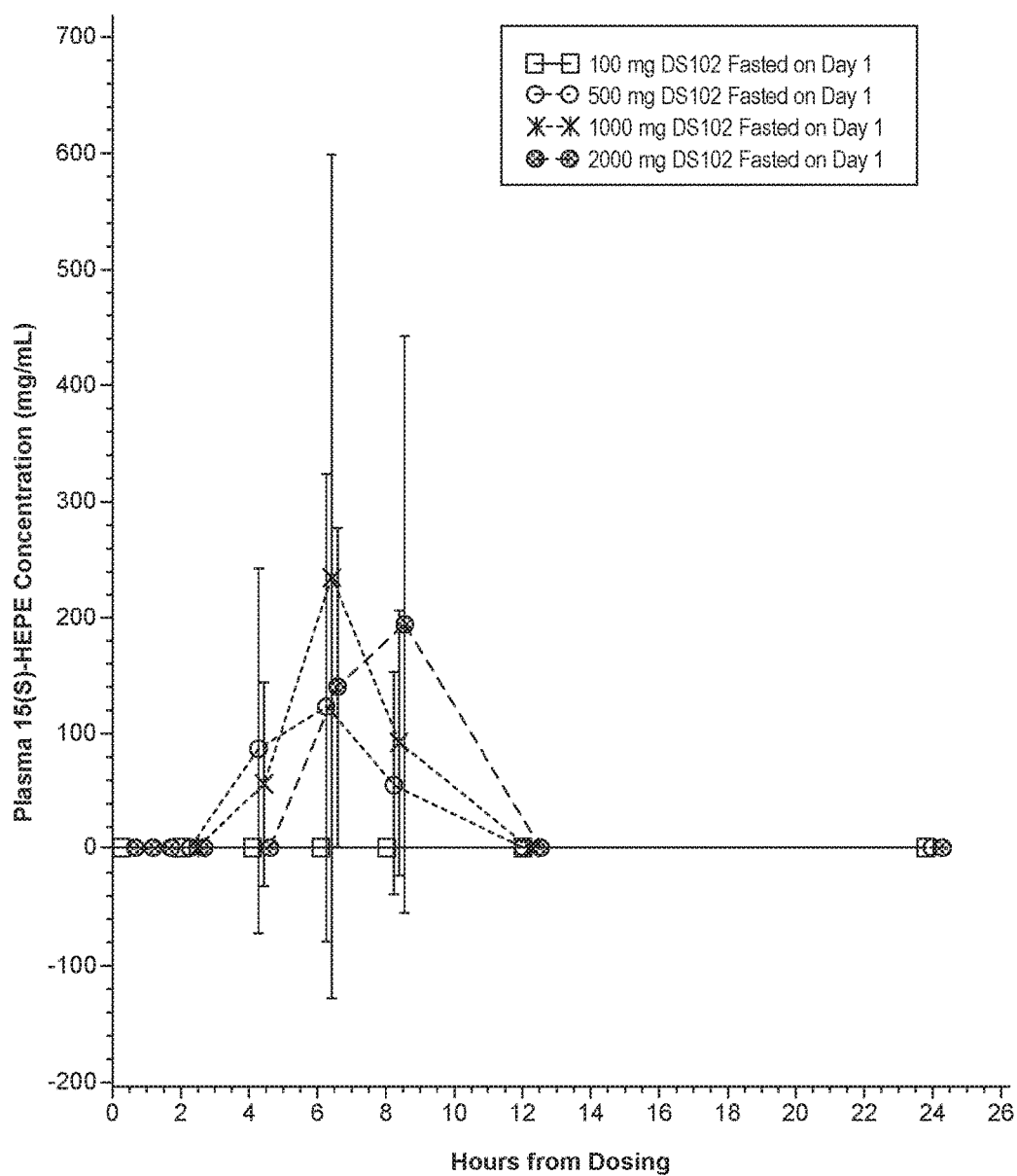
FIG. 1 graphically illustrates mean plasma concentrations of 15-Hydroxy-Eicosapentaenoic Acid Ethyl Ester [15(S)-HEPE] following a single oral dose of 100 mg, 500 mg, 1000 mg, and 2000 mg DS102, under fasted conditions.

In various embodiments, the invention provides compositions and formulations comprising 15-HEPE and methods of treating diseases and disorders using the same.

As used herein, "15-HEPE" is 15-Hydroxy-eicosa-5,8,11,13,17-pentaenoic acid. 15-HEPE, also occasionally referred to as 15-OHEPA, can be synthesized from eicosapentaenoic acid ("EPA," eicosa-5,8,11,14,17-pentaenoic acid or 20:5n-3), an omega-3 fatty acid according to methods known in the art. As used herein, the term "15-HEPE" refers to 15-HEPE in its free acid form (e.g, 15-hydroxy-eicosa-5,8,11,13,17-pentaenoic acid) and/or a pharmaceutically acceptable ester, conjugate or salt thereof, or mixtures of any of the foregoing. A derivative of 15-HEPE may be used instead, though this does not include any derivative compound missing the hydroxy group of 15-HEPE. In some embodiments, the 15-HEPE is used in the free acid form. Alternatively, pharmaceutically acceptable esters or salts of 15-HEPE are used in the invention. In some embodiments, the 15-HEPE is in the form of a $C_{1-4}$ alkyl ester such as methyl ester or ethyl ester form.

In another aspect, the present invention provides a pharmaceutical composition comprising a therapeutically effective amount of 15-HEPE. The 15-HEPE may be the sole significant active ingredient in that composition and in the methods and uses as stated herein. The 15-HEPE may be the sole active ingredient. Alternatively, the 15-HEPE may be combined for co-formulation or co-administration with other agents.

In one embodiment, 15-HEPE or a composition comprising 15-HEPE is administered to a fed subject. A "fed subject" or a subject in a "fed state" herein refers to a subject who has had a meal within the proceeding 4 hours.

15-HEPE is a chiral molecule and may be used in the (S)- or (R)-enantiomeric form, or as a racemic mixture. Used herein, "15-HEPE" includes all such forms, with no limitation as to stereospecifcity. In another embodiment, the 15-HEPE comprises the (S) form: 15(S)-Hydroxy-(5Z,8Z,11Z,13E,17Z)-eicosapentaenoic acid. In some embodiments, the 15-HEPE may be used in the form of the ethyl ester. In other embodiments, the 15-HEPE may be used as the free acid.

The present invention further provides a pharmaceutical composition for oral delivery, comprising 15-HEPE. That composition may comprise a pharmaceutically acceptable excipient. The 15-HEPE may be in any form as discussed herein. The 15-HEPE may be present from about 50 mg to about 3000 mg.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only, and are not intended to be limiting.

Other features and advantages of the invention will be apparent from the following detailed description. While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

15-Hydroxy Eicosapentaenoic Acid

In one embodiment, compositions of the invention comprise 15-HEPE as an active ingredient. 15-HEPE is the abbreviation for 15-Hydroxy eicosapentaenoic acid, a metabolite of eicosapentaenoic acid (EPA) that can be synthesized via methods known in the art, such as exposure of eicospentaenoic acid to the enzyme 15-lipoxygenase. As used herein, the term "15-HEPE" refers to 15-HEPE in its free acid form (e.g., 15-Hydroxy eicosapentaenoic acid) and/or a pharmaceutically acceptable ester, conjugate or salt thereof, or mixtures of any of the foregoing. A derviative of 15-HEPE may be used instead, though this does not include any derivative compound missing the hydroxy group of 15-HEPE. The term "pharmaceutically acceptable" in the present context means that the substance in question does not produce unacceptable toxicity to the subject or interaction with other components of the composition.

In one embodiment, the 15-HEPE is in the form of an ester (also referred to herein as E-15-HEPE or ethyl-15-HEPE). In another embodiment, the 15-HEPE comprises a $C_1$-$C_5$ alkyl ester of 15-HEPE. In another embodiment, the 15-HEPE comprises 15-HEPE methyl ester, 15-HEPE propyl ester, or 15-HEPE butyl ester. In still another embodiment, the 15-HEPE comprises the optically active 15(S)-Hydroxy-(5Z,8Z,11Z,13E,17Z)-eicosapentaenoic acid. This isomer may be used in any of the forms discussed above.

In another embodiment, the 15-HEPE comprises lithium 15-HEPE, mono, di- or triglyceride 15-HEPE or any other ester or salt of 15-HEPE, or the free acid form of 15-HEPE.

In various embodiments, the invention provides pharmaceutical compositions, for example orally deliverable compositions, comprising 15-HEPE. In one embodiment, the compositions comprise a therapeutically effective amount of 15-HEPE. In one embodiment, the pharmaceutical composition comprises about 0.1% to about 99%, about 1')/0 to about 95%, about 5% to about 90% by weight of 15-HEPE.

In one embodiment, the pharmaceutical composition comprises about at least about 70%, at least about 80% or at least about 90%, by weight, of 15-HEPE. In one embodiment, the pharmaceutical composition comprises at least about 50%, at least about 60%, at least about 70%, at least about 80% or at least about 90%, by weight of 15-HEPE.

In another embodiment, 15-HEPE is present in a composition of the invention in an amount of about 1 mg to about 10,000 mg, 25 mg to about 7500 mg, about 25 mg to about 5000 mg, about 50 mg to about 5000 mg, about 50 mg to about 3000 mg, about 75 mg to about 2500 mg, or about 100 mg to about 1000 mg, for example about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, or about 2500 mg.

In one embodiment, 15-HEPE present in a composition of the invention comprises at least 90% by weight 15-HEPE (as the term "15-HEPE" is defined and exemplified herein). 15-HEPE compositions can comprise even higher purity 15-HEPE, for example at least 95% by weight 15-HEPE or at least 97% by weight 15-HEPE, wherein the 15-HEPE is any form of 15-HEPE as set forth herein. The purity of 15-HEPE can further be defined (e.g. impurity profile) by any of the descriptions of 15-HEPE provided herein.

Above are discussed the amounts of the 15-HEPE in the pharmaceutical composition and their purity. The nature of the essential fatty acids and their synthesis is such that the 15-HEPE composition may include moieties from other essential fatty acids in the essential fatty acid metabolic cascade.

In one embodiment, a composition of the invention contains not more than about 10%, not more than about 9%, not more than about 8%, not more than about 7%, not more than about 6%, not more than about 5%, not more than about 4%, not more than about 3%, not more than about 2%, not more than about 1° A, or not more than about 0.5%, by weight of other omega-3 fatty acids including alpha linolenic acid, stearidonic acid, docosahexaenoic acid (DHA) or derivatives thereof. In other embodiments there is substantially no, or no such other omega-3 fatty acids present.

In another embodiment, 15-HEPE represents at least about 60%, at least about 70%, at least about 80%, at least about 90%, at least about 95%, at least about 97%, at least about 98%, at least about 99%, or 100%, by weight, of all fatty acids present in a composition of the invention.

There may be present some residual eicosapentaenoic acid from the synthesis of the 15-HEPE. There may be, not more than about 10%, not more than about 9%, not more than about 8%, not more than about 7%, not more than about 6%, not more than about 5%, not more than about 4%, not more than about 3%, not more than about 2%, not more than about 1° A, or not more than about 0.5%, by weight EPA. Alternatively, there is substantially no, or some EPA in a form which has not been modified to the hydroxyl-form.

Dosage Forms

A composition for use in accordance with the disclosure can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In some embodiments, compositions of the invention are in the form of orally deliverable dosage forms or units. Non-limiting examples of suitable dosage forms include tablets (e.g. suspension tablets, bite suspension tablets, rapid dispersion tablets, chewable tablets, etc), caplets, capsules (e.g. a soft or a hard gelatin capsule or HPMC capsule), lozenges, sachets, cachets, troches, pellets, suspension, elixirs, syrups or any other solid dosage form reasonably adapted for oral administration. The terms "oral delivery" and "oral administration" herein include any form of delivery wherein the agent or composition is placed in the mouth of the subject under treatment, whether swallowed or not. This therefore includes buccal and sublingual administration, as well as esophagael administration.

Alternatively, compositions of the invention can also be formulated for rectal, topical, or parenteral (e.g. subcutaneous, intramuscular, intravenous and intradermal or infusion) delivery.

In discussing the amount of 15-HEPE in a composition of the invention, this may be split over several dosage forms. There is a limit as to the size for oral administration. If a subject is to be administered 1 to 4 g 15-HEPE a day, this may be by up to 4 capsules, each providing 1 g of 15-HEPE.

Compositions of the invention can be in the form of liquid dosage forms or dose units to be imbibed directly or they can be mixed with food or beverage prior to ingestion. Non-limiting examples of suitable liquid dosage forms include solutions, suspensions, elixirs, syrups, liquid aerosol formulations, and the like.

In another embodiment, compositions of the invention comprise one or more pharmaceutically acceptable excipients. The term "pharmaceutically acceptable excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition, and that does not produce unacceptable toxicity or interaction with other components in the composition. By way of example only, a pharmaceutical composition according to the present disclosure may comprise one or more of: antioxidants, surfactants, preservatives, flavouring agents, co-solvents, viscosity aids, suspension aids, and lipophilic phases.

In one embodiment, the pharmaceutical composition comprises one or more antioxidants such as ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, niacinamide, and the like. In one embodiment, the pharmaceutical composition comprises about 0.01 wt. % to about 2 wt. % of an antioxidant, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, about 0.5 wt. %, about 0.51 wt. %, about 0.52 wt. %, about 0.53 wt. %, about 0.54 wt. %, about 0.55 wt. %, about 0.56 wt. %, about 0.57 wt. %, about 0.58 wt. %, about 0.59 wt. %, about 0.6 wt. %, about 0.61 wt. %, about 0.62 wt. %, about 0.63 wt. %, about 0.64 wt. %, about 0.65 wt. %, about 0.66 wt. %, about 0.67 wt. %, about 0.68 wt. %, about 0.69 wt. %, about 0.7 wt. %, about 0.71 wt. %, about 0.72 wt. %, about 0.73 wt. %, about 0.74 wt. %, about 0.75 wt. %, about 0.76 wt. %, about 0.77 wt. %, about 0.78 wt. %, about 0.79 wt. %, about 0.8 wt. %, about 0.81 wt. %, about 0.82 wt. %, about 0.83 wt. %, about 0.84 wt. %, about 0.85 wt. %, about 0.86 wt. %, about 0.87 wt. %, about 0.88 wt. %, about 0.89 wt. %, about 0.9 wt. %, about 0.91 wt. %, about 0.92 wt. %, about 0.93 wt. %, about 0.94 wt. %, about 0.95 wt. %, about 0.96 wt. %, about 0.97 wt. %, about 0.98 wt. %, about 0.99 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. % of the one or more antioxidant.

Therapeutic Methods

The compositions and formulations disclosed herein may be used in the treatment of a liver disease, arthritis, fibrosis, idiopathic pulmonary fibrosis, impaired insulin sensitivity, psoriasis, cancer (e.g. melanoma), neurodegenerative disorders (e.g. Huntington's disease), inflammatory diseases, adipocyte differentiation, fertility or reproduction issues, pain, obesity, and their sequelae.

In one embodiment, the present disclosure provides a method of treating and/or preventing impaired insulin sensitivity in a subject, the method comprising administering to the subject an effective amount of a composition comprising 15-HEPE. In some embodiments, the method further comprises determining that the subject is sensitive to insulin and/or is at risk of developing insulin sensitivity before administering the composition comprising 15-HEPE.

In one embodiment, the present disclosure provides a method of treating and/or preventing psoriasis in a subject, the method comprising administering to the subject an effective amount of a composition comprising 15-HEPE. In some embodiments, the method further comprises determining that the subject has psoriasis and/or is at risk of developing psoriasis before administering the composition comprising 15-HEPE.

In one embodiment, the present disclosure provides a method of treating and/or preventing cancer in a subject, the method comprising administering to the subject an effective amount of a composition comprising 15-HEPE. In some embodiments, the method further comprises determining that the subject has cancer and/or is at risk of developing cancer before administering the composition comprising 15-HEPE. In some embodiments, the cancer is a skin cancer. In some embodiments, the skin cancer is melanoma.

In one embodiment, the present disclosure provides a method of treating and/or preventing a neurodegenerative disorder in a subject, the method comprising administering to the subject an effective amount of a composition comprising 15-HEPE. In some embodiments, the method further comprises determining that the subject has a neurodegenerative disorder and/or is at risk of developing a neurodegenerative disorder before administering the composition comprising 15-HEPE. In some embodiments, the neurodegenerative disorder is Huntington's disease.

In one embodiment, the present disclosure provides a method of treating and/or preventing an inflammatory disease in a subject, the method comprising administering to the subject an effective amount of a composition comprising 15-HEPE. In some embodiments, the method further comprises determining that the subject has an inflammatory disease and/or is at risk of developing an inflammatory disease before administering the composition comprising 15-HEPE.

In one embodiment, the present disclosure provides a method of treating and/or preventing an adipocyte differentiation disorder in a subject, the method comprising administering to the subject an effective amount of a composition comprising 15-HEPE. In some embodiments, the method further comprises determining that the subject has an adipocyte differentiation disorder and/or is at risk of developing an adipocyte differentiation disorder before administering the composition comprising 15-HEPE.

In one embodiment, the present disclosure provides a method of treating and/or preventing fertility or reproduction issues in a subject, the method comprising administering to the subject an effective amount of a composition comprising 15-HEPE. In some embodiments, the method further comprises determining that the subject has fertility or reproduction issues and/or is at risk of developing fertility or reproduction issues before administering the composition comprising 15-HEPE.

In one embodiment, the present disclosure provides a method of treating and/or preventing pain in a subject, the method comprising administering to the subject an effective amount of a composition comprising 15-HEPE. In some embodiments, the method further comprises determining that the subject has pain and/or is at risk of developing pain before administering the composition comprising 15-HEPE.

In one embodiment, the present disclosure provides a method of treating and/or preventing obesity in a subject, the method comprising administering to the subject an effective amount of a composition comprising 15-HEPE. In some embodiments, the method further comprises determining that the subject is obese and/or is at risk of becoming obese before administering the composition comprising 15-HEPE.

In one embodiment, the present disclosure provides a method of treating and/or preventing idiopathic pulmonary fibrosis in a subject, the method comprising administering to the subject an effective amount of a composition comprising 15-HEPE. In some embodiments, the method further comprises determining that the subject has idiopathic pulmonary fibrosis and/or is at risk of developing idiopathic pulmonary fibrosis before administering the composition comprising 15-HEPE.

As used herein, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

An "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician. The term "pharmaceutically acceptable" in the present context means that the substance in question does not produce unacceptable toxicity to the subject or interaction with other components of the composition.

Without further description, it is believed that one of ordinary skill in the art may, using the preceding description and the following illustrative examples, make and utilize the agents of the present disclosure and practice the claimed methods and compositions. The following examples are intended to illustrate various embodiments of the present technology. As such, the specific embodiments discussed are not to be construed as limitations on the scope of the present technology. It will be apparent to one skilled in the art that various equivalents, changes, and modifications may be made without departing from the scope of the present technology, and it is understood that such equivalent embodiments are to be included herein. Non-limiting examples of compositions comprising 15-HEPE that may be used with methods of the present technology are described herein. Further, all references cited in the disclosure are hereby incorporated by reference in their entirety, as if fully set forth herein. The following working examples are provided to facilitate the practice of the present disclosure, and are not to be construed as limiting in any way the remainder of the disclosure.

Example

A Phase I, single-centre, randomised, double-blind, placebo-controlled study in male and female healthy volunteers aged 18 to 45 years, inclusive was performed. Fifty-seven (57) subjects were enrolled with 8 subjects per cohort (ideally 4 males and 4 females, but no less than 3 per gender). Cohort 5 enrolled a total of 9 subjects to account for discontinued subjects. The effective date of study commencement was defined as inclusion of the first subject (inclusion starts with the informed consent signature). Subjects who were enrolled in Part 1 of the study (single dose cohorts) could have been brought back and re-enrolled in Part 2 (multiple dose) provided they had no AEs related to the study drug and that there was at least a 14-day washout period before starting the multiple dose. There were 18 subjects who participated in both study parts. The subjects underwent screening within 21 days prior to study Day 1.

Part 1—Single Ascending Dose (SAD)

Part 1 comprised 4 dose cohorts (100 mg, 500 mg, 1000 mg, and 2000 mg). Six (6) subjects were randomized to receive DS102 and 2 subjects received matching placebo. A single oral dose of DS102 or matching placebo was administered.

Part 1—Food Effect

Cohort 2 also received 500 mg of DS102 in 2 fed states. While the first 500 mg dose was given in fasted state, the second and third 500 mg doses were given in fed state (standard ATPIII/TLC diet and high-fat diet, respectively). The second dose was received at least 14 days after their first dose and the third dose was received at least 14 days after their second dose.

Part 2—Multiple Ascending Doses (MAD)

Part 2 of the study involved a multipledose regimen at 3 dose levels using 3 cohorts consisting of 8 subjects each. Six (6) subjects were randomized to receive DS102 and 2 subjects received matching placebo. Cohorts 5 and 6 (9 and 8 subjects, respectively) received oral DS102 or placebo QD for 28 days.

Cohorts (for Part 1) commenced in a sequential manner starting with the first 3 cohorts (100 mg, 500 mg, and 1000 mg) in parallel with matching placebo. A minimum of 5 subjects with 8 days evaluable safety data from the 1000 mg cohort were required before the decision was made on commencing to the next cohort (2000 mg single dose) and before commencing the first cohort in Part 2 (up to 500 mg/day).

A total of 49 subjects (32 subjects in Part 1(24 active and 8 placebo) and 17 subjects in Part 2 (13 active and 4 placebo)) entered the study and were randomized to study treatment. A total of 47 subjects completed the study. All subjects were included for safety analysis. All 37 subjects who received DS102 were included in the PK analysis. All subjects enrolled in this study were judged by the Principal Investigator (PI) to be normal, healthy volunteers who met all inclusion and none of the exclusion criteria.

In Part 1, DS102 capsules (Lot No. 2540M-1504) or matching placebo (Lot No. KM73) were administered in a single oral dose according to Table 1.

TABLE 1

Administration of DS102 and Placebo Capsules According to Part 1.

| Cohort | DS102 Dose | DS102 Dosage | Fed/Fasted |
|---|---|---|---|
| 1 | 100 mg | 1 × 100 mg DS102 or Placebo Capsule | Fasted |
| 2 | 500 mg | 1 × 500 mg DS102 or Placebo Capsules | Fasted |
| 3 | 1000 mg | 2 × 500 mg DS102 or Placebo Capsules | Fasted |
| 4 | 2000 mg | 4 × 500 mg DS102 or Placebo Capsules | Fasted |
| 2 | 500 mg | 1 × 500 mg DS102 or Placebo Capsules | Fed (Standard ATPIII/TLC Diet) |
| 2 | 500 mg | 1 × 500 mg DS102 or Placebo Capsules | Fed (High Fat Diet) |

In Part 2, DS102 capsules (Lot No. 2540M-1504) or matching placebo (Lot No. KM73) were administered QD for 28 days according to Table 2.

TABLE 2

Administration of DS102 and Placebo Capsules According to Part 2.

| Cohort | DS102 Dose | DS102 Dosage | Fed/Fasted |
|---|---|---|---|
| 5 | 500 mg | 1 × 500 mg DS102 or Placebo Capsules QD | Fasted |
| 6 | 1000 mg | 2 × 500 mg DS102 or Placebo Capsules QD | Fasted |
| 7 | 2000 mg | 4 × 500 mg DS102 or Placebo Capsules QD | Fasted |

Planned study duration for clinical conduct was 12 weeks. The total duration of participation, including the screening period for each subject, was approximately 4 weeks for Cohorts 1, 3, and 4 and 7 weeks for Cohort 2 in study Part 1. The total duration of participation, including the screening period for each subject, was approximately 9 weeks for Cohorts 5 and 6 in study Part 2.

Pharmacokinetics:

For study Part 1, Cohorts 1, 2, 3, and 4 blood samples were taken predose on Day 1 up to 312 hours postdose. For study Part 2, Cohorts 5, 6, and 7 blood samples were taken on Days 1, 14, and 28 at predose and up to 168 hours postdose. The appropriate PK parameters, e.g., Cmax, Tmax, AUC0-24, AUC0-last, AUC0-inf, AUC % ext, Kel, t½, RCmax, and RAUC were presented, where appropriate. Plasma 15(S)-HEPE data contained many values below the limit of quantitation (BLQ) and only sparse measurable concentrations leading to incomplete PK profiles. Given the nature of the data observed, conventional dose proportionality and steady-state analyses could not be performed. No inferential statistical analyses were performed for PK parameters.

Statistical Methods:

Summary statistics, including sample size (N), arithmetic mean (mean), standard deviation (SD), coefficient of variation (CV %), median, minimum, and maximum were calculated for all nominal concentration time points. Plasma 15(S)-HEPE PK parameters were tabulated by treatment and listed by subject and parameter. Summary statistics (N, mean, SD, CV %, median, minimum, and maximum) were calculated for plasma 15(S)-HEPE PK parameters. In addition, geometric mean (Geom. Mean) and geometric CV % (Geom. CV %) were presented for AUCs and Cmax. Excluded subjects were included in the PK parameter table listings, but were excluded from the summary statistics and noted as such in the tables. Mean and individual concentration-time profiles were presented on linear and semi-log scales. Linear mean plots were presented with and without SD. Individual plots were presented on linear and semi-log scales.

Safety:

All clinical safety data were presented in by-subject data listings. Safety was evaluated by clinical laboratory tests, physical examination, vital signs, electrocardiograms (ECGs), and adverse events (AEs).

Continuous variables were summarized using number of observations (N), mean, SD, median, minimum, and maximum. Frequency counts were reported for categorical data. AEs were classified according to the Medical Dictionary for Regulatory Activities (MedDRA®), Version 18.0. Concomitant medications were classified according to the World Health Organization (WHO) Drug Dictionary 1 Mar. 2015. Vital sign, ECG, and laboratory summary and change from baseline results were presented. Shift tables were also presented for laboratory and ECG parameters.

Mean plasma concentrations of 15-Hydroxy-Eicosapentaenoic Acid Ethyl Ester [15(S)-HEPE] following a single oral dose of 100 mg, 500 mg, 1000 mg, and 2000 mg DS102, under fasted conditions, are presented in FIG. 1.

Concentration-time profiles of 15(S)-HEPE in plasma were not well characterized following single oral administration of 100 mg, 500 mg, 1000 mg, or 2000 mg DS102 under fasted conditions. Plasma concentrations following 100 mg DS102 were BLQ over the entire sampling interval, for all subjects. Only 2 subjects had quantifiable plasma concentrations following 500 mg DS102, 3 subjects following 1000 mg, and 4 subjects following 2000 mg (of which 1 had only 1 measurable concentration). Mean plasma concentrations were highly variable.

Figure 2:
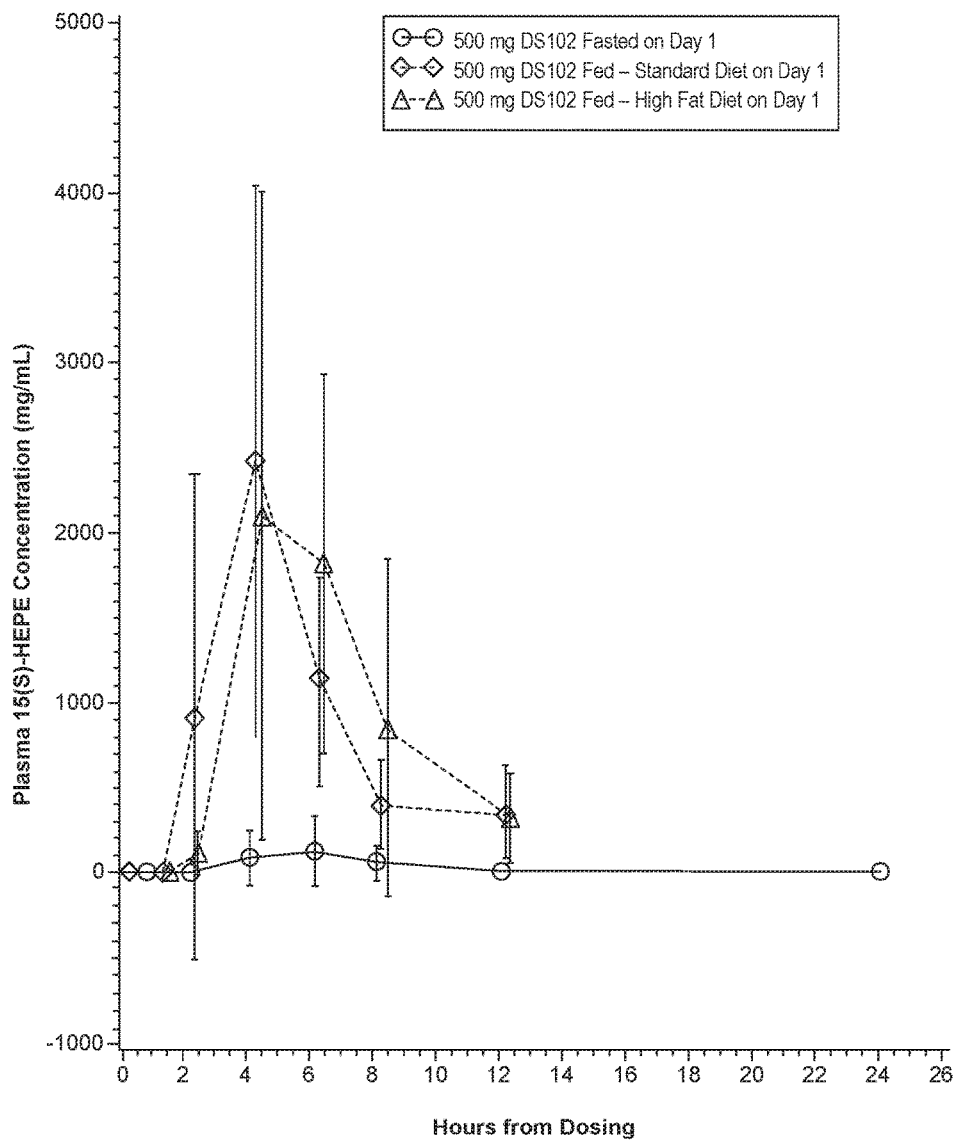
FIG. 2 graphically illustrates mean plasma 15(S)-HEPE concentrations following a single oral dose of 500 mg DS102 (15-HEPE) under fasted and fed conditions.

Mean plasma 15(S)-HEPE concentrations following a single oral dose of 500 mg DS102 under fasted and fed conditions, are presented in FIG. 2.

Figure 3:
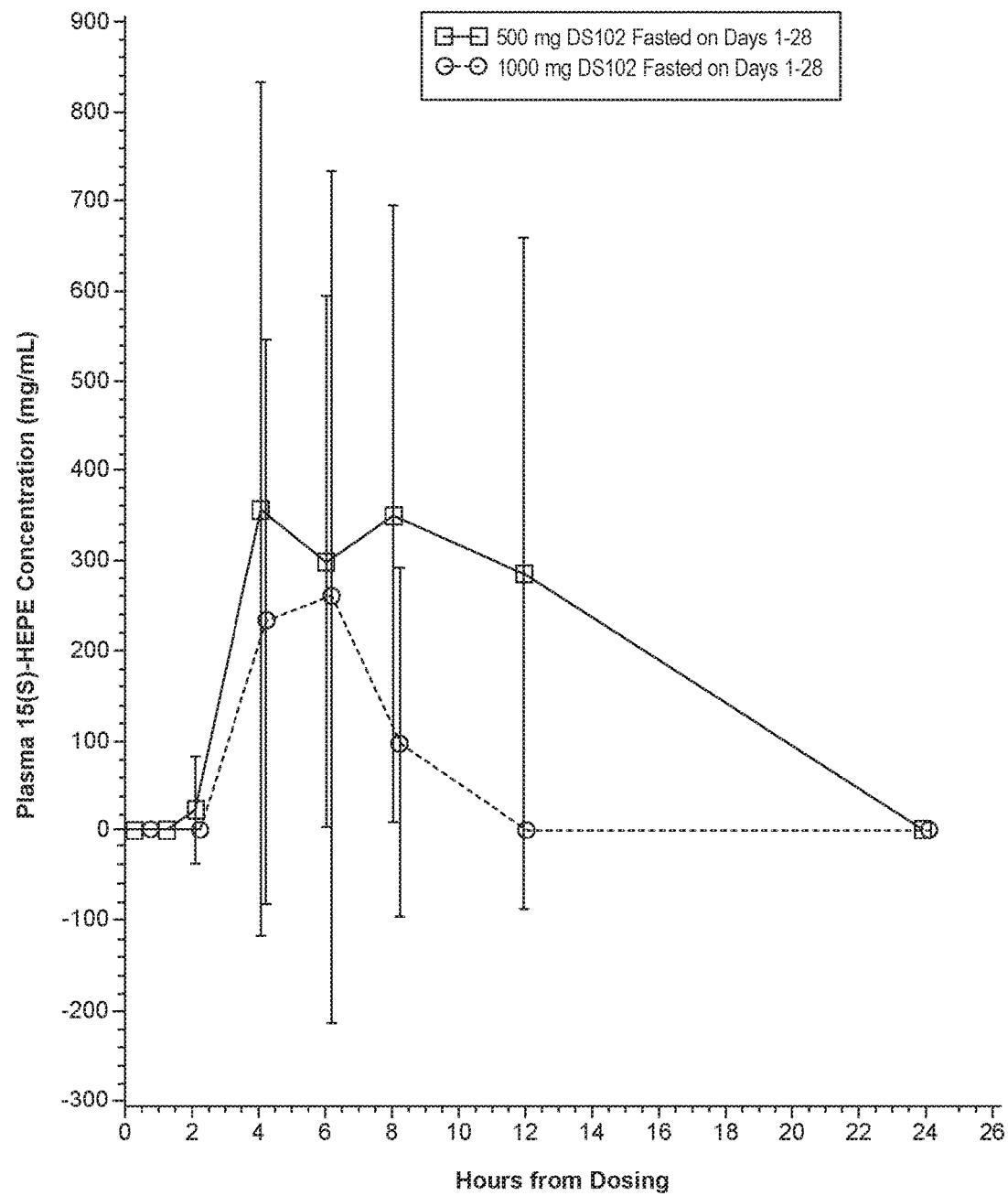
FIG. 3 graphically illustrates mean plasma 15(S)-HEPE concentrations following multiple oral QD doses of 500 mg and 1000 mg for 28 days, under fasted conditions, at day 1 of 28.
Figure 4:
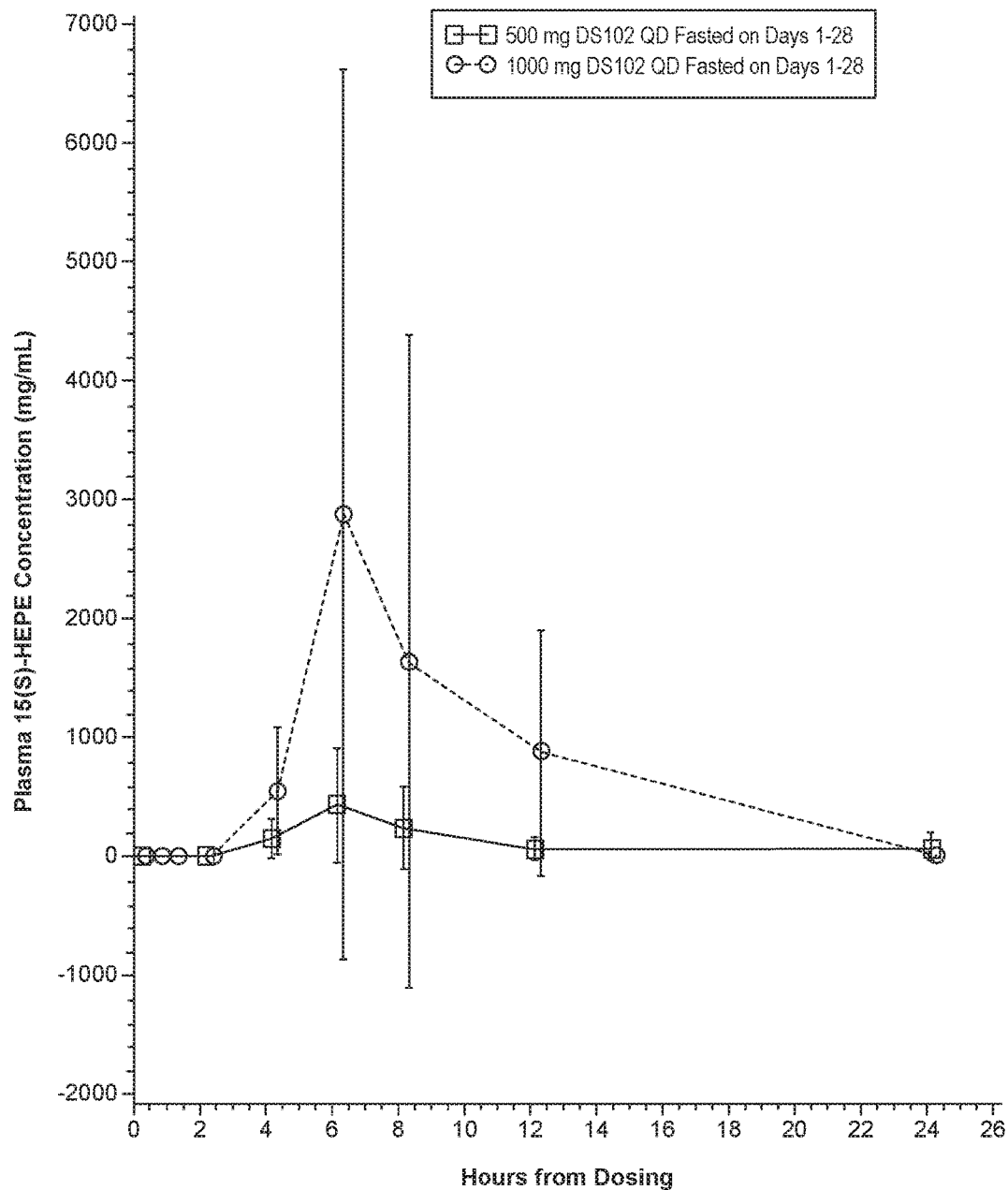
FIG. 4 graphically illustrates mean plasma 15(S)-HEPE concentrations following multiple oral QD doses of 500 mg and 1000 mg for 28 days, under fasted conditions, at day 14 of 28.
Figure 5:
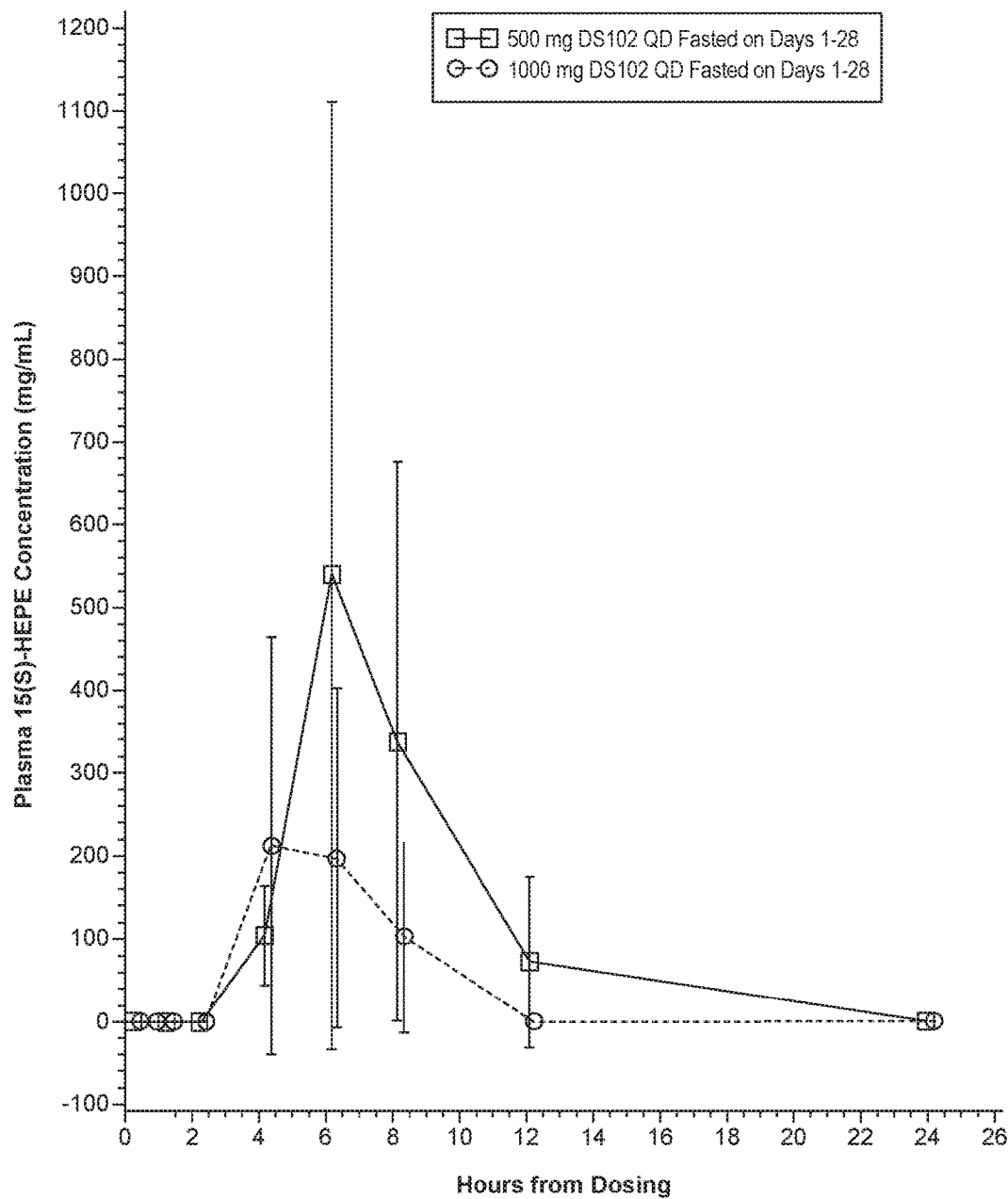
FIG. 5 graphically illustrates mean plasma 15(S)-HEPE concentrations following multiple oral QD doses of 500 mg and 1000 mg for 28 days, under fasted conditions, at day 28 of 28.

When 500 mg of DS102 was administered with a standard or high-fat diet, concentration-time profiles of 15(S)-HEPE in plasma were characterized for all subjects. Mean plasma concentrations of 15(S)-HEPE were higher under fed conditions compared to fasted conditions. Peak mean concentrations were reached at approximately 4 hours following 500 mg DS102, with a standard or high-fat diet, followed by an apparently rapid decline with plasma concentrations that remained quantifiable in at least one subject for 12 hours postdose. There was no significant difference between 15(S)-HEPE profiles from subjects on a standard or high-fat diet, but results were also considerably variable. Mean plasma 15(S)-HEPE concentrations following multiple oral QD doses of 500 mg and 1000 mg for 28 days, under fasted conditions, at days 1, 14, and 28 are presented in FIGS. 3, 4, and 5, respectively.

Concentration-time profiles of 15(S)-HEPE in plasma were not well characterized following multiple oral QD doses of 500 mg and 1000 mg DS102 for 28 days; mean plasma concentrations remained highly variable. Following 500 mg DS102 QD, mean plasma 15(S)-HEPE concentrations were highly variable, but generally similar for all days. Predose values (troughs) were not quantifiable on Days 14 and 28. Peak mean 15(S)-HEPE concentrations tended to increase with study day from 4 hours on Day 1 to 6 hours on Days 14 and 28, followed by an apparently rapid decline, with plasma concentrations that remained measurable in at least one subject through 12 hours postdose on Days 1 and 28 and through 24 hours postdose on Day 14. Following 1000 mg DS102 QD, mean plasma 15(S)-HEPE concentrations were higher on Day 14 than on Days 1 and 28. There were no quantifiable predose values (troughs) on Days 14 and 28. Time to peak mean concentrations ranged from 4 to 6 hours, with plasma 15(S)-HEPE concentrations that remained quantifiable in at least one subject through 8 hours postdose on Days 1 and 28 and through 12 hours postdose on Day 14. These results are presented in Table 3.

TABLE 3

Pharmacokinetic Parameters Following More Than One Dose of DS102.

| Pharmacokinetic Parameters | 100 mg Fasted (N = 0) | 500 mg Fasted (N = 2) | 1000 mg Fasted (N = 3) | 2000 mg Fasted (N = 3) |
|---|---|---|---|---|
| AUC0-24 (ng * hr/mL)$^a$ | — | — | — | — |
| AUC0-last (ng * hr/mL)$^a$ | — | 1270 (70.9) | 1063 (102.6) | 733.3 (56.5) |
| AUC0-inf (ng * hr/mL)$^a$ | — | — | — | — |
| AUC % extrap (ng * hr/mL)$^b$ | — | — | — | — |
| Cmax (ng/mL)$^a$ | — | 343.7 (52.1) | 366.2 (102.5) | 294.3 (70.1) |
| Tmax (hr)$^c$ | — | 6.005 (6.00, 6.01) | 5.996 (5.99, 6.00) | 8.001 (6.01, 8.01) |
| Tlast (hr)$^c$ | — | 8.001 (8.00, 8.00) | 7.999 (8.00, 8.00) | 8.001 (8.00, 8.01) |
| Kel (1/hr)$^b$ | — | — | — | — |
| t½ (hr)$^b$ | — | — | — | — |

100 mg DS102 fasted on Day 1
500 mg DS102 fasted on Day 1
1000 mg DS102 fasted on Day 1
2000 mg DS102 fasted on Day 1
$^a$Presented as geom. mean (geom. CV %)
$^b$Presented as mean ± SD
$^c$Presented as median (minimum, maximum)
—: Not reportable.
PK parameters were not calculable for any subject following 100 mg Fasted.
PK parameters were not calculable for Subjects 9, 12, 15, and 16 following 500 mg Fasted.
PK parameters were not calculable for Subjects 20, 23, and 24 following 1000 mg Fasted.
PK parameters were not calculable for Subjects 29, 31, and 32 following 2000 mg Fasted.

As shown in Table 3, the median Tmax values were 6.00 hours for both the 500 mg and 1000 mg dose levels and 8.00 hours for the 2000 mg dose level. For all 3 cohorts in the fasted state, PK parameters were only calculated for the 2 or 3 subjects with sufficient data. Exposure parameters (Cmax and AUC0-last) were highly variable and should be interpreted with caution, with geometric mean coefficient of variation (CV %) above 50%.

TABLE 4

Pharmacokinetic Parameters Following a Single Dose of DS102.

| Pharmacokinetic Parameters | 500 mg Fasted (N = 2) | 500 mg Fed Standard Diet (N = 6) | 500 mg Fed High Fat Diet (N = 6) |
|---|---|---|---|
| AUC0-24 (ng * hr/mL)$^a$ | — | 10940 (17.9) | — |
| AUC0-last (ng * hr/mL)$^a$ | 1270 (70.9) | 8450 (67.7) | 9693 (51.9) |
| AUC0-inf (ng * hr/mL)$^a$ | — | 11050 (19.7) | — |
| AUC % extrap (ng * hr/mL)$^b$ | — | 7.543 ± 9.7728 | — |
| Cmax (ng/mL)$^a$ | 343.7 (52.1) | 2420 (62.1) | 2402 (64.7) |
| Tmax (hr)$^c$ | 6.005 (6.00, 6.01) | 4.014 (2.00, 6.01) | 6.021 (4.00, 7.99) |
| Tlast (hr)$^c$ | 8.001 (8.00, 8.00) | 8.017 (8.00, 12.00) | 11.993 (8.00, 12.01) |
| Kel (1/hr)$^b$ | — | 0.4711 ± 0.22828 | — |
| t½ (hr)$^b$ | — | 1.998 ± 1.5155 | — |

500 mg DS102 fasted on Day 1
500 mg DS102 fed-standard diet on Day 1
500 mg DS102 fed-high fat diet on Day 1
$^a$Presented as geom. mean (geom. CV %)
$^b$Presented as mean ± SD
$^c$Presented as median (minimum, maximum)
—: Not reportable.
PK parameters were not calculable for Subjects 9, 12, 15 and 16 following 500 mg Fasted.

As shown in Table 4, the median Tmax values following single-dose administration of 500 mg DS102 after a standard and high-fat diet were 4.00 hours and 6.00 hours, respectively. For both treatment regimens, PK parameters were calculated for the 6 subjects who received DS102, except for AUC0-inf and t½ which were calculable for only 4 subjects following a standard diet.

doses (1000 mg and 2000 mg) under fasted conditions. Compared to when DS102 was given with a standard diet, the apparition of 15(S)-HEPE in plasma given with a high-fat diet was delayed by 2 hours. Due to the high variability, it was not possible to determine if the extent of exposure was different following a high-fat versus standard diet using noncompartmental methods.

TABLE 5

Pharmacokinetic Parameters at Days 1, 14, and 28.

| | 500 mg QD - Fasted | | |
|---|---|---|---|
| Pharmacokinetic Parameters | Day 1 (N = 6)* | Day 14 (N = 3) | Day 28 (N = 2) |
| AUC0-24 (ng * hr/mL)$^a$ | 6249 | — | — |
| AUC0-last (ng * hr/mL)$^a$ | 1681 (156.6) | 2370 (106.8) | 2787 (92.6) |
| AUC0-inf (ng * hr/mL)$^a$ | 6277 | — | — |
| AUC % extrap (ng * hr/mL)$^b$ | 9.411 | — | — |
| Cmax (ng/mL)$^a$ | 459.1 (119.5) | 644.1 (68.3) | 737.4 (67.9) |
| Tmax (hr)$^c$ | 5.005 (4.00, 8.14) | 5.995 (5.99, 6.01) | 6.004 (6.00, 6.01) |
| Tlast (hr)$^c$ | 8.079 (6.00, 12.00) | 8.034 (8.00, 12.00) | 10.002 (8.01, 12.00) |
| Kel (1/hr)$^a$ | 0.2455 | — | — |
| t½ (hr)$^a$ | 2.824 | — | — |
| RAUC$^b$ | — | 6.807 ± 10.322 | 8.205 ± 10.210 |
| RCmax$^b$ | — | 4.177 ± 5.4055 | 5.923 ± 6.8329 |

500 mg DS102 QD fasted on Days1-28
$^a$: Presented as geom. mean (geom. CV %)
$^b$: Presented as mean ± SD
$^c$: Presented as median (minimum, maximum)
—: Not reportable.
*AUC0-24, AUC0-inf, AUC % extrap, Kel, and t½ were reported only for Subject 38.
PK parameters were not calculable for Subjects 34, 37, and 39 on Day 14.
PK parameters were not calculable for Subjects 34, 37, 39, and 138 on Day 28.

As shown in Table 5, following a standard diet, the mean 15(S)-HEPE t½ was 2.00 hours. No clear elimination phase was apparent following a high-fat diet. Though data were highly variable, it was apparent that a standard or high-fat diet increased mean maximum and overall exposure of 15(S)-HEPE (based on Cmax and AUC0-last, respectively) relative to the fasted condition. Moreover, 15(S)-HEPE exposure following a single oral dose of 500 mg DS102 appeared higher under fed conditions relative to higher Safety Results.

There were no deaths, serious adverse events (SAEs), or subject discontinuations due to AEs reported in this study. No trend was observed in single or multiple ascending doses of DS102 with regard to subject incidence for AE reporting and was comparable to AE reporting following placebo. The PI considered the majority of events to be mild in intensity and not related to the study treatment. The majority of the events reported were considered not related to the study treatment with events of dysguesia and eructation (following DS102 treatment) considered related. There were several laboratory events reported as AEs during the study in Parts 1 and 2. All laboratory reported events were mild in intensity and considered not related to the study treatment.

Single ascending doses of 100 mg, 500 mg, 1000 mg and 2000 mg DS102 and multiple ascending doses of 500 mg, 500 and 1000 mg were safe and well tolerated in the healthy subjects in this study.

PK profiles of 15(S)-HEPE in healthy subjects following single oral administration of 100 mg, 500 mg, 1000 mg, or 2000 mg DS102 and following multiple oral QD administration of 500 mg or 2000 mg DS102 in the fasted state could not be well characterized due to the lack of quantifiable concentrations and variability.

Administration of DS102 in a fed state (standard or high-fat diet) appeared to considerably increase 15(S)-HEPE absorption.

The terminal elimination phase was generally not apparent following single and multiple doses in the fasted state. Mean t½ w estimated to be 2.0 hours in subjects who received a standard diet.

Results across dose levels studied in the single and multiple dose cohorts are not indicative of a predictable exposure, one that increases proportionally with increasing dose.

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain embodiments of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Reference herein to "one embodiment," "an embodiment," or similar formulations means that a particular feature of a composition, a composition, a method, or a characteristic described in connection with the embodiment can be included in at least one embodiment of the present technology. Thus, the appearances of such phrases or formulations herein are not necessarily all referring to the same embodiment. Furthermore, various particular features, compositions, methods, or characteristics may be combined in any suitable manner in one or more embodiments.

From the foregoing, it will be appreciated that specific embodiments of the invention have been described herein for purposes of illustration, but that various modifications may be made without deviating from the scope of the invention. Accordingly, the invention is not limited except as by the appended claims.

What is claimed is:

1. A pharmaceutical composition comprising a pharmaceutically acceptable ester, conjugate, and/or salt of 15-HEPE.

2. The composition of claim 1, wherein the pharmaceutical composition comprises 100 mg to 1000 mg of the pharmaceutically acceptable ester, conjugate, and/or salt of 15-HEPE and the pharmaceutically acceptable ester, conjugate, and/or salt of 15-HEPE comprises at least about 50%, by weight, of the pharmaceutical composition.

3. The composition of claim 1, wherein the 15-HEPE is in esterified form.

4. The composition of claim 3, wherein the esterified form is a methyl ester form, an ethyl ester form, or a combination thereof.

5. The composition of claim 3, wherein the esterified form is a triglyceride form.

6. The composition of claim 1, wherein the 15-HEPE is in salt form.

* * * * *